United States Patent
Bsharim et al.

(10) Patent No.: US 10,744,032 B2
(45) Date of Patent: Aug. 18, 2020

(54) INSTRUMENT FOR EXTRACTING NUCLEUS OF EYE LENS DURING CATARACT SURGERY

(71) Applicant: MOR RESEARCH APPLICATIONS LTD., Tel Aviv (IL)

(72) Inventors: Eliyahu Bsharim, Beer Sheva (IL); Tova Lifshitz, Lehavim (IL); Nadav Yaakov Belfair, Omer (IL)

(73) Assignee: MOR RESEARCH APPLICATIONS LTD., Tel Aviv (IL)

( * ) Notice: Subject to any disclaimer, the term of this patent is extended or adjusted under 35 U.S.C. 154(b) by 164 days.

(21) Appl. No.: 15/775,515

(22) PCT Filed: Nov. 10, 2016

(86) PCT No.: PCT/IL2016/051211
§ 371 (c)(1),
(2) Date: May 11, 2018

(87) PCT Pub. No.: WO2017/081683
PCT Pub. Date: May 18, 2017

(65) Prior Publication Data
US 2018/0333299 A1 Nov. 22, 2018

Related U.S. Application Data

(60) Provisional application No. 62/254,200, filed on Nov. 12, 2015.

(51) Int. Cl.
*A61F 9/007* (2006.01)
(52) U.S. Cl.
CPC ...... *A61F 9/00736* (2013.01); *A61F 9/00745* (2013.01)

(58) Field of Classification Search
CPC .. A61F 9/008; A61F 9/00736; A61F 9/00745; A61F 9/00754; A61F 9/00709;
(Continued)

(56) References Cited

U.S. PATENT DOCUMENTS

| 4,428,748 A | 1/1984 | Peyman et al. |
| 4,655,219 A * | 4/1987 | Petruzzi ................. A61B 1/018 |
| | | 606/206 |

(Continued)

FOREIGN PATENT DOCUMENTS

| CN | 1430487 | 7/2003 |
| CN | 202714968 U | 2/2013 |

(Continued)

OTHER PUBLICATIONS

Supplementary European Search Report, Application No. 16863782.5-1124/3373872, dated Jun. 6, 2019, 7 pages.

(Continued)

*Primary Examiner* — Katrina M Stransky
(74) *Attorney, Agent, or Firm* — The Roy Gross Law Firm, LLC; Roy Gross

(57) ABSTRACT

An ophthalmic surgical instrument for fragmenting the lens nucleus of an eye, and method of use thereof. The instrument includes an elongated handle portion, a tubular head portion at the handle portion distal end, at least three prongs with cutting tips, and a holding ring. The prongs are selectively retractable into and deployable from the head portion. The holding ring selectively contracts and expands to adjust the deployment width of the prongs. The instrument is inserted toward the eye lens through a corneal incision, while the head portion is opened to deploy the prongs to slide over and grasp onto the lens nucleus at a posterior position thereof. The instrument is then withdrawn toward the eye lens anterior while the head portion is closed to retract the (Continued)

prongs, such that the prong cutting tips cut along the lens nucleus, so as to fragment the lens nucleus into multiple segments.

8 Claims, 3 Drawing Sheets

(58) Field of Classification Search
CPC .............. A61F 9/007; A61B 18/1447; A61B 2017/301; A61B 2017/305
See application file for complete search history.

(56) References Cited

U.S. PATENT DOCUMENTS

| | | | |
|---|---|---|---|
| 4,869,716 | A | 9/1989 | Smirmaul |
| 7,186,258 | B2 | 3/2007 | Sabet |
| 8,313,507 | B2 * | 11/2012 | Ravikumar ........ A61B 17/0218 606/205 |
| 8,475,480 | B2 | 7/2013 | Mackool |
| 2003/0040773 | A1 * | 2/2003 | Arumi .................... A61B 17/29 606/205 |
| 2003/0088253 | A1 | 5/2003 | Seil |
| 2008/0188877 | A1 | 8/2008 | Hickingbotham |
| 2013/0102955 | A1 | 4/2013 | Koplin |

FOREIGN PATENT DOCUMENTS

| | | |
|---|---|---|
| WO | 0189401 | 11/2001 |
| WO | 03039335 | 5/2003 |
| WO | 2005092258 A1 | 10/2005 |
| WO | 2010068467 | 6/2010 |
| WO | 2013048976 | 4/2013 |

OTHER PUBLICATIONS

International Search Report PCT/IL2016/051211 Completed: Feb. 12, 2017; dated Feb. 12, 2017 3 pages.
Written Opinion of the International Searching Authority PCT/IL2016/051211 dated Feb. 12, 2017 4 pages.
Chinese Office Action and Search Report, Chinese Application No. 201680066000.9, dated Dec. 23, 2019.

* cited by examiner

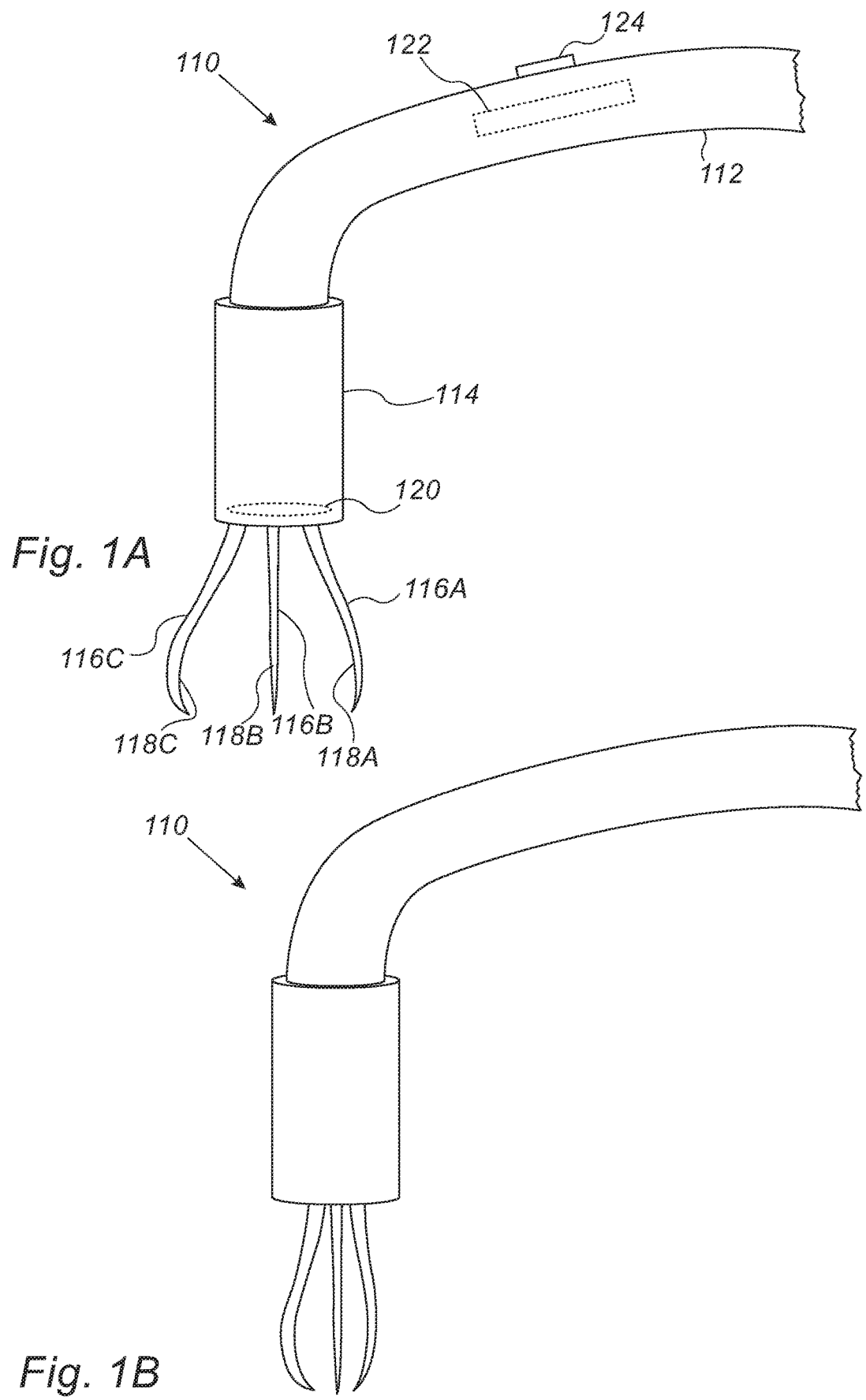

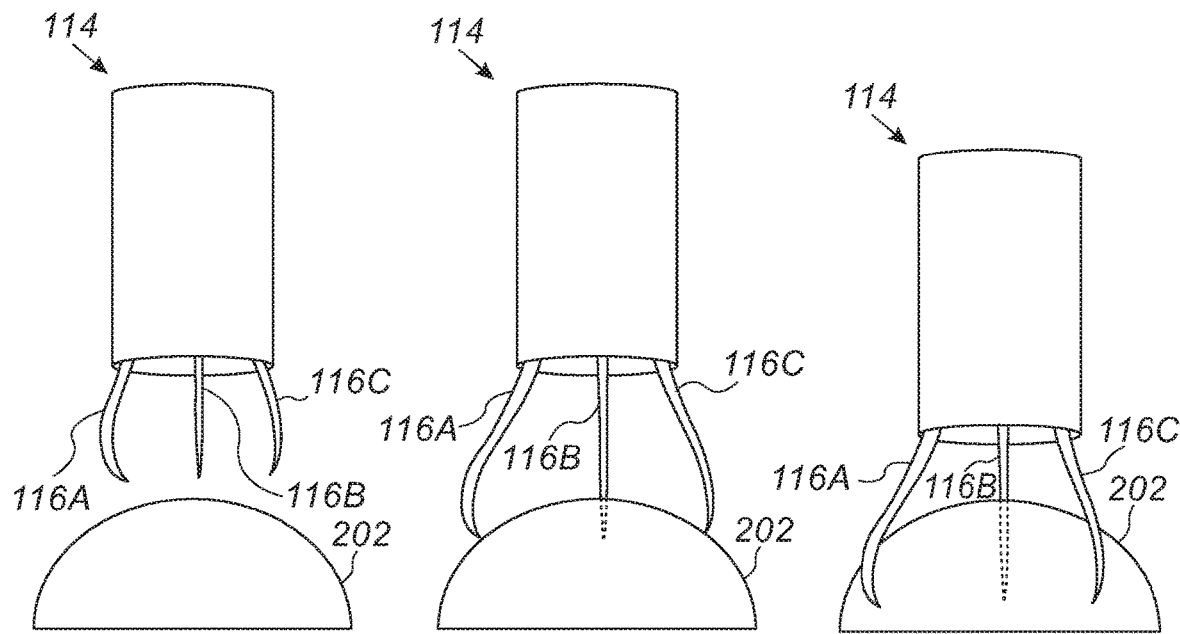
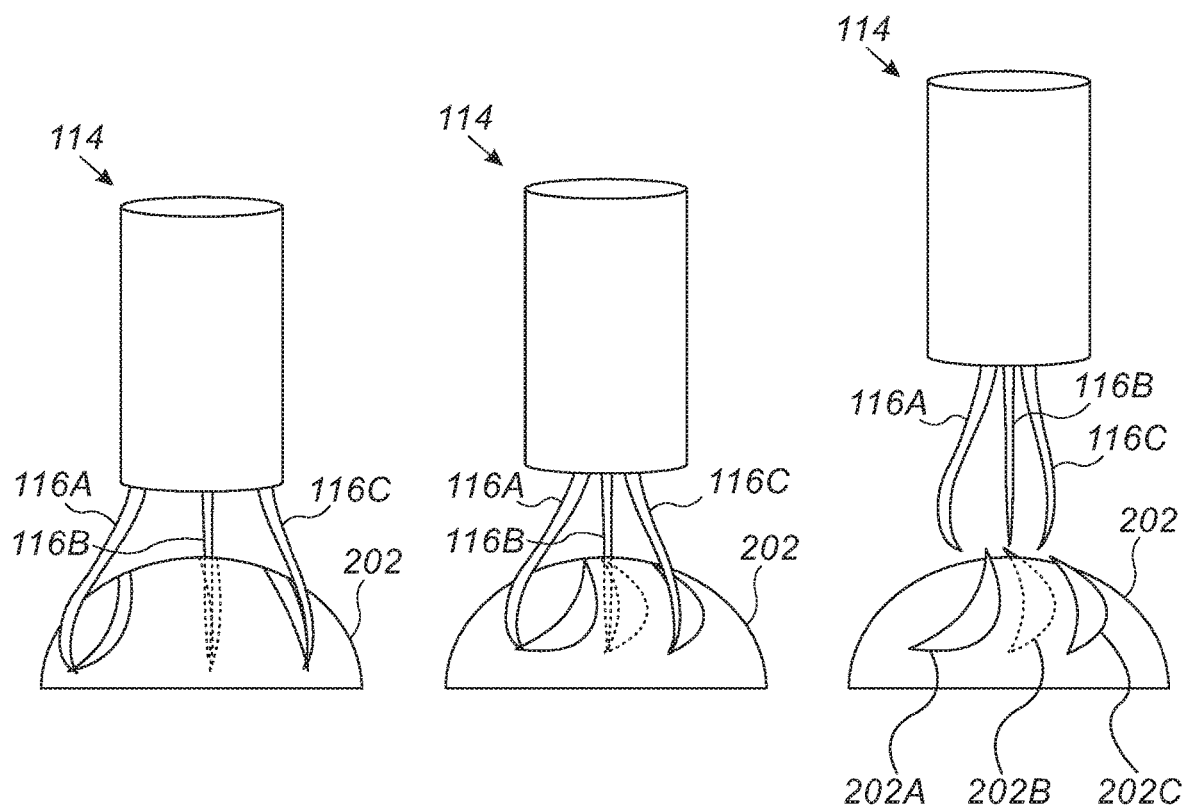

INSTRUMENT FOR EXTRACTING NUCLEUS OF EYE LENS DURING CATARACT SURGERY

RELATED APPLICATIONS

This application is a National Phase of PCT Patent Application No. PCT/IL2016/051211 having an International filing date of Nov. 10, 2016, which claims the benefit of priority of U.S. Provisional Application No. 62/254,200 entitled INSTRUMENT FOR EXTRACTING NUCLEUS OF EYE LENS DURING CATARACT SURGERY filed on Nov. 12, 2015. The contents of the above applications are all incorporated by reference as if fully set forth herein in their entirety.

FIELD

Embodiments disclosed herein relate to ophthalmology in general, and to medical devices utilized in cataract surgeries in particular.

BACKGROUND

Vision impairment and vision loss is a common affliction associated with aging. As a person grows older, a gradual deterioration of eyesight tends to develop as a result of various genetic and environmental factors. One of the most widespread forms of eye degeneration is a cataract, in which the normally clear lens of the eye becomes cloudy, thereby hindering normal vision. In particular, a buildup of protein or pigment in the lens obstructs the transmission of incoming light through the lens and onto the retina portion of the eye. Since new lens cells form on the outside of the lens, all the older cells are compacted into the center of the lens resulting in clouding or "opacification". The severity of a cataract can vary, ranging from reduced visual acuity and impaired recognition, such as objects that appear cloudy or with substantial glare, and extending to partial or even complete loss of vision (blindness).

Cataract surgery involves the removal of the natural eye lens and its replacement with an artificial intraocular lens implant. There are a number of different surgical techniques presently in use, one of which is known as "phacoemulsification". Phacoemulsification involves initially forming an incision in the cornea to gain access to the interior of the eye, followed by the formation of a circular opening in the anterior lens capsule (known as an "anterior capsulorhexis") to allow for removal of the cataract. The next step is fragmentation of the lens nucleus ("nucleus chopping"), followed by emulsification and extraction of the lens material. The fragmentation process, which is intended to facilitate the emulsification, may be conducted mechanically using at least a fine instrument that accesses the lens nucleus from a side port (i.e., a different incision from the main capsulotomy incision). Other techniques for nucleus fragmentation utilize the application of radiation by a femtosecond laser device (which may also be used for the corneal incision and/or the anterior capsulorhexis). A dedicated femtosecond laser device requires costly equipment that typically cost hundreds of thousands of dollars.

SUMMARY

In accordance with aspects of the embodiments, there is thus provided an ophthalmic surgical instrument for fragmenting the lens nucleus of an eye. In an embodiment, the instrument includes at least: an elongated handle portion, a tubular head portion, at least three prongs, and an internal holding ring. The head portion is disposed at a distal end of the elongated handle portion. In an embodiment, each of the prongs includes a cutting tip. In an embodiment, the prongs are selectively retractable into and deployable from the head portion. In an embodiment, the holding ring is configured to selectively contract and expand to adjust the deployment width of the prongs. During the insertion of the instrument toward the eye lens through a corneal incision, the head portion is opened to deploy the prongs to slide over and grasp onto the lens nucleus at a posterior position thereof. During the withdrawal of the instrument toward the anterior of the eye lens, the head portion is closed to retract the prongs, such that the cutting tips of the prongs cut along the lens nucleus, so as to fragment the lens nucleus into multiple segments. The surgical instrument may further include a vibration mechanism configured to selectively vibrate the prongs. The vibration mechanism may be activated during the insertion of the instrument toward the eye lens, and/or during the withdrawal of the instrument toward the anterior of the eye lens. The prongs may be arc-shaped. The prongs may include a shape-memory material.

In accordance with another aspect, there is thus provided a method for fragmenting the lens nucleus of an eye. The method includes the procedure of providing an ophthalmic surgical instrument that includes at least: an elongated handle portion, a tubular head portion, at least three prongs, and an internal holding ring. The head portion is disposed at a distal end of the elongated handle portion. In an embodiment, each of the prongs includes a cutting tip. In an embodiment, the prongs are selectively retractable into and deployable from the head portion. In an embodiment, the holding ring is configured to selectively contract and expand to adjust the deployment width of the prongs. The method further includes the procedure of inserting the instrument toward the eye lens through a corneal incision, while opening the head portion to deploy the prongs to slide over and grasp onto the lens nucleus at a posterior position thereof. The method further includes the procedure of withdrawing the instrument toward the anterior of the eye lens, while closing the head portion to retract the prongs, such that the cutting tips of the prongs cut along the lens nucleus, so as to fragment the lens nucleus into multiple segments. The method may further include activating a vibration mechanism of the surgical instrument, the vibration mechanism configured to selectively vibrate the prongs. The vibration mechanism may be activated during the insertion of the instrument toward the eye lens, and/or during the withdrawal of the instrument toward the anterior of the eye lens.

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

BRIEF DESCRIPTION OF THE DRAWINGS

The embodiments will be understood and appreciated more fully from the following detailed description taken in conjunction with the drawings in which:

FIG. 1A is a schematic illustration of an ophthalmic surgical instrument for fragmenting the lens nucleus of a human eye during a cataract surgery, constructed and operative in accordance with an embodiment;

FIG. 1B is a schematic illustration of the surgical instrument of FIG. 1A with the prongs partially retracted, constructed and operative in accordance with an embodiment;

FIG. 4A is a perspective-view schematic illustration of an initial stage of the eye lens fragmentation process performed using the surgical instrument of FIG. 1A, operative in accordance with an embodiment;

FIG. 4B is a perspective-view schematic illustration of a subsequent sequential stage of the eye lens fragmentation process performed using the surgical instrument of FIG. 1A, operative in accordance with an embodiment;

FIG. 4C is a perspective-view schematic illustration of a further subsequent sequential stage of the eye lens fragmentation process performed using the surgical instrument of FIG. 1A, operative in accordance with an embodiment;

FIG. 4D is a perspective-view schematic illustration of yet a further subsequent sequential stage of the eye lens fragmentation process performed using the surgical instrument of FIG. 1A, operative in accordance with an embodiment;

FIG. 4E is a perspective-view schematic illustration of another subsequent sequential stage of the eye lens fragmentation process performed using the surgical instrument of FIG. 1A, operative in accordance with an embodiment; and FIG. 4F is a perspective-view schematic illustration of yet another subsequent sequential stage of the eye lens fragmentation process performed using the surgical instrument of FIG. 1A, operative in accordance with an embodiment.

DETAILED DESCRIPTION OF THE EMBODIMENTS

Figure 2A:
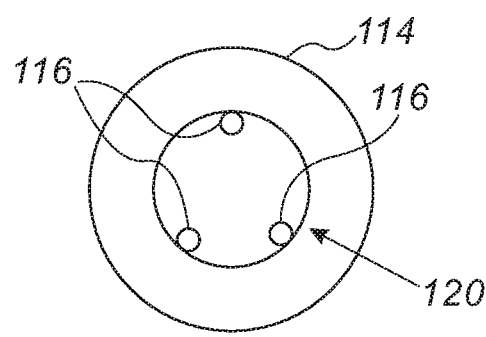
FIG. 2A is a schematic illustration of a cross-sectional view through the tubular head portion of the surgical instrument of FIG. 1A when the head portion is in an expanded state, operative in accordance with an embodiment.

Disclosed embodiments provide an instrument for fragmenting the eye lens nucleus during a, for example, phacoemulsification type cataract surgery procedure. In an embodiment, the instrument includes three or more arc-shape prongs deployable outward from, and retractable into, a head portion at the distal end of the instrument. When the instrument is inserted into the eye, the prongs are deployed to slide over and grasp onto the lens nucleus. The prongs may include cutting tips with sharpened and, optionally jagged, edges, allowing the prongs to cut the nucleus while the instrument is pulled back away from the lens and the prongs are retracted, so as to fragment or break up the nucleus into multiple segments simultaneously. The instrument may further include a vibrating mechanism, to allow selective vibration of the prongs during the insertion of the instrument into the lens material as well as when pulling back the instrument, in order to facilitate the initial penetration and fragmentation processes. The term 'lens nucleus' as used herein may encompass any nucleus portion, including but not limited to the "endonucleus" or the "embryonic nucleus".

Reference is now made to FIG. 1A, which is a schematic illustration of an ophthalmic surgical instrument, generally referenced 110, for fragmenting the lens nucleus of a human eye during a cataract surgery, constructed and operative in accordance with an embodiment. Surgical instrument 110 includes an elongated handle portion 112, a tubular head portion 114, at least three prongs 116A, 116B, 116C, a holding ring 120, optionally a vibration mechanism 122, and a control dial 124.

Elongated handle portion 112 is configured to allow a user of surgical instrument 110 (e.g., a surgeon or other medical professional) to comfortably hold instrument 110. Handle portion 112 may include a rubber hand grip or a supplementary coating or accessory to facilitate grasping by the user. Alternatively, surgical instrument 110 may be held by an automated or remote-controlled robotic or machine component during at least certain stages of the surgical process.

Each of prongs 116A, 116B, 116C is substantially concave or arc-shaped, with a respective sharpened blade on its inner edge and a respective sharpened cutting tip 118A, 118B, 118C. In particular, prongs 116A, 1116B, 116C each have an inwardly curved concave shape relative to a longitudinal axis of instrument 110, i.e., the inwardly curved surface is facing the longitudinal axis. Alternatively, the prongs may be substantially straight. For example, the prongs can have two or more straight sections such as to form an angular and arcuate shape. The cutting blade of prongs 116A, 116B, 116C may be plain edged and/or at least partially serrated or jagged edged.

Figure 2B:
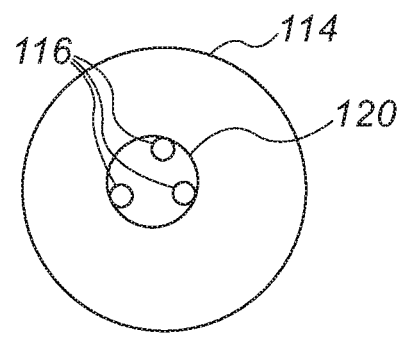
FIG. 2B is a schematic illustration of a cross-sectional view through the tubular head portion of the surgical instrument of FIG. 1A when the head portion is in a contracted state, operative in accordance with an embodiment.

Tubular head portion 114 extends from the distal end of handle portion 112 (i.e., furthest away from the hand of the user). Head portion 114 may engage with prongs 116A, 116B, 116C in a manner that allows for selectively retracting or deploying prongs 116A, 116B, 116C. In particular, when the distal opening of head portion 114 is contracted or "closed" (i.e., when the opening diameter is decreased), prongs 116A, 116B, 116C are configured to retract inwards into head portion 114, e.g., such that the tips of the prongs do not extend beyond the (distal) edge of head portion 114, and such that the prongs are positioned closer together to one another. The shifting of head portion 114 into an expanded or "opened" position (i.e., the diameter of the distal opening is increased), urges prongs 116A, 116B, 116C to deploy outwards (e.g., by means of a spring mechanism), such that the prongs are positioned out and to the sides, further apart from one another, and extending beyond the edge of head portion 114. Reference is made to FIG. 1B, which is a schematic illustration of surgical instrument 110 with the prongs partially retracted. Reference is further made to FIGS. 2A and 2B, which illustrate cross-sectional views through the tubular head portion 114 of surgical instrument 110 when the head portion 114 is in an expanded state (FIG. 2A), and when the head portion 114 is in a contracted state (FIG. 2B), respectively.

Holding ring 120 may be situated within tubular head portion 114, and clasps around at least part of prongs 116A, 116B, 116C. Holding ring 120 allows for adjusting the penetration diameter, by adjusting the degree to which the prongs 116A, 116B, 116C are deployed outwards. For example, increasing the diameter of holding ring 120 serves to increase the deployment width of prongs 116A, 116B, 116C, and thus widen the diameter occupied by surgical instrument 110 during its penetration into the eye lens. Conversely, decreasing the diameter of holding ring 120 shortens the deployment width of prongs 116A, 116B, 116C, thereby decreasing the diameter occupied by surgical instrument 110 during its penetration into the eye lens. The deployment width of prongs 116A, 116B, 116C also influences the spacing between the fragmented nucleus portions. The user can thus adjust the diameter of holding ring 120 to select the desired deployment width (within the available physical limits) in accordance with the operational requirements.

Vibration mechanism 122 is situated within surgical instrument 110, such as embedded within elongated handle portion 122, and is configured to selectively vibrate prongs 116A, 116B, 116C. Vibration mechanism 122 may be embodied by any suitable components configured to induce a vibrating effect, such as a vibration motor circuit or similar electromechanical units known in the art. Control dial 124 allows a user to control or adjust settings, parameters or modes associated with surgical instrument 110. For example, adjustment of dial 124 may selectively open and close head portion 114 (to retract or deploy prongs 116A, 116B, 116C), or alternatively may activate and deactivate vibration mechanism 122. Accordingly, dial 124 may be embodied by a plurality of separate dials, knobs or buttons (or alternative input interfaces, such as a digital interface) dedicated to different functions.

Surgical instrument 110 may optionally include and/or be associated with additional components not shown in FIG. 1A, for enabling the implementation of the disclosed subject matter. For example, surgical instrument may also include (or be coupled with) a power supply (not shown), such as batteries for providing power to vibration mechanism 122. Surgical instrument 110 may also include a user interface (not shown) for providing visual or auditory feedback, such as to provide an indication of current operational modes or settings associated with surgical instrument (e.g., whether vibration mechanism 122 is currently activated; whether holding rings 120 are contracted or expanded; and the like).

Figure 3:
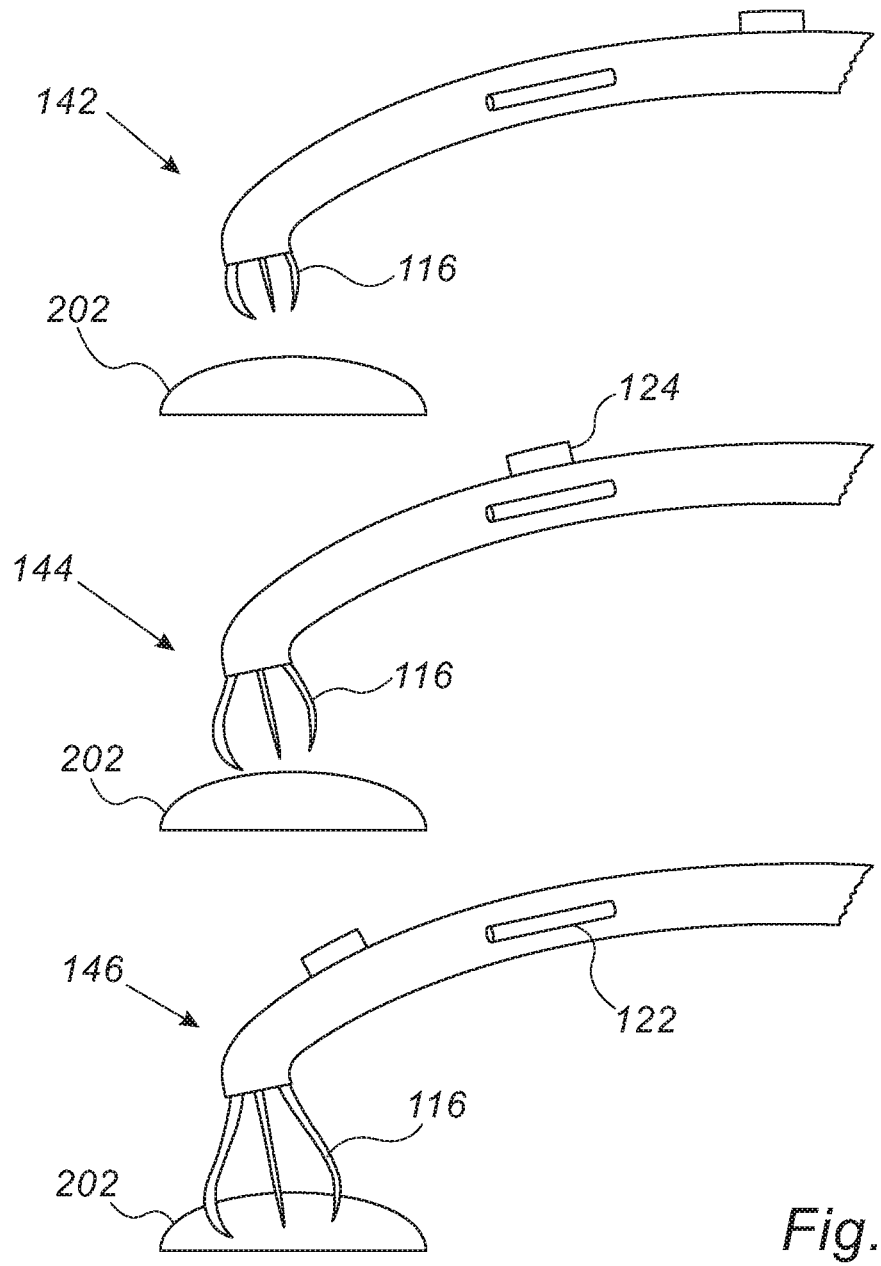
FIG. 3 is a side-view schematic illustration of the surgical instrument undergoing a sequence of stages when grasping the eye lens prior to fragmentation, operative in accordance with an embodiment.

The operation of surgical instrument 110 will now be discussed in the context of a medical practitioner performing a cataract surgery procedure. The medical practitioner will be considered herein as the user of surgical instrument 110. Reference is now made to FIG. 3, which is a side-view schematic illustration of the surgical instrument undergoing a sequence of stages when grasping the eye lens prior to fragmentation, operative in accordance with an embodiment. In a first stage, referenced 142, the user inserts instrument 110 into the eye of the patient toward the lens, such as via a corneal incision and an anterior lens capsule opening formed beforehand. While advancing instrument 110 toward the lens nucleus, referenced 202, the user gradually deploys prongs 116 by adjusting holding ring 120 accordingly (e.g., via dial 124), as shown in second stage 144. As the instrument advances even closer toward lens nucleus 202, prongs are fully deployed and are maneuvered to encompass and grasp lens nucleus 202, as shown in third stage 126. The lens nucleus fragmentation process utilizing surgical instrument 110 will be elaborated upon further hereinbelow.

Reference is now made to FIGS. 4A through 4F, which depict perspective-view schematic illustrations of sequential stages of the eye lens fragmentation process performed using the surgical instrument of FIG. 1A, operative in accordance with an embodiment. Referring to FIG. 4A, instrument 110 is inserted into the eye toward the lens while prongs 116A, 116B, 116C are initially in a retracted state and positioned substantially within head portion 114 at the distal end of instrument 110. Vibration mechanism 122 (not shown) may optionally be activated in order to facilitate the insertion of instrument 110, for example, in order that instrument will not apply undue pressure against the zonules. Referring to FIG. 4B, the user gradually deploys prongs 116A, 116B, 116C to extend outwards from head portion 114, by opening head portion 114, until prongs 116A, 116B, 116C come into contact with the anterior of the lens nucleus 202. The penetration diameter occupied by instrument 110 (or, correspondingly, the deployment width of prongs 116A, 116B, 116C) may be selectively adjusted by increasing or decreasing the diameter of holding ring 120, as necessary. Referring to FIG. 4C, the user maneuvers instrument 110 forward such that the (vibrating) prongs 116A, 116B, 116C slide over the surface of lens nucleus 202 until reaching a position in which the prongs 116A, 116B, 116C are securely grasping and clamped onto nucleus 202. In particular, prong tips 118A, 118B, 118C engage with lens nucleus at separate points at the posterior of lens nucleus 202 and approximately equidistantly spaced apart, such that the prongs 116A, 116B, 116C substantially encompass nucleus 202. The opening of head portion 114 may be implemented gradually such that prong tips 118A, 118B, 118C reach the posterior edge of nucleus 202 as prongs 116A, 116B, 116C reach a fully deployed state. The vibration of prongs 116A, 116B, 116C may facilitate the initial penetration of surgical instrument 110 to the eye lens and clamping of nucleus 202, without applying adverse pressure on the zonules. The prongs 116A, 116B, 116C generally do not cut through nucleus 202 during this forward motion prior to clamping, although slight incisions may form as prongs 116A, 116B, 116C slide forward, while the cutting tips 118A, 118B, 188C may penetrate into and become embedded within nucleus 202.

Referring to FIG. 4D, after prongs 116A, 116B, 116C have securely grasped lens nucleus 202, the user may activate vibration mechanism 122 to induce the vibration of prongs 116A, 116B, 116C (if the vibration was not activated previously during the insertion stage). Referring to FIG. 4E, the user pulls back surgical instrument 110 (i.e., away from the eye lens) while retracting prongs 116A, 116B, 116C by closing head portion 114, causing the cutting tips 118A, 118B, 118C of the (vibrating) prongs 116A, 116B, 116C to slice through the nucleus. The actual cutting or fragmentation of nucleus 202 occurs during the pulling back motion together with the retraction of prongs 116A, 116B, 116C, which are driven inwards toward one another following their inwardly curved concave shape, e.g., in a "clasping" type motion. The vibration of prongs 116A, 1166, 116C may serve to facilitate and augment the cutting process, which is primarily implemented by the sharpened tips 118A, 1186, 118C as the prongs 116A, 1166, 116C are pulled back along nucleus 202 in an anterior direction while following a clasping motion. Eventually the prongs 116A, 1166, 116C fully traverse the nucleus 202, resulting in the division of nucleus 202 into multiple smaller fragments, referenced 202A, 2026, 202C, where the fragment boundaries are delineated along the cutting path of prongs 116A, 1166, 116C, as shown in FIG. 4F. Finally, the retracted prongs 116A, 1166, 116C are withdrawn fully back into head portion 114 of surgical instrument 110.

The aforementioned process may optionally be repeated multiple times, such as if a single insertion and withdrawal of surgical instrument 110 (i.e., involving the prongs 116A, 1166, 116C grasping and encompassing nucleus 202 followed by vibrating/cutting) does not sufficiently or fully fragment nucleus 202 after a single pass. For example, the fragmentation may be repeated so as to generate at least six to eight separate nucleus fragments, rather than merely the three fragments formed after the initial pass. Following the fragmentation of lens nucleus 202 with surgical instrument 110, the nucleus fragments may then be extracted using a phacoemulsification suction instrument, and the cataract surgery proceeds accordingly.

Prongs 116A, 1166, 116C may optionally be composed at least partially from a shape-memory material, such as a copper/aluminum/nickel/titanium alloy, such that a structural deformation of the prongs is maintained during the operation of surgical instrument 110. For example, the size and shape of prongs 116A, 1166, 116C may be initially modeled to conform with the size and shape of a standard eye lens nucleus.

It is further noted that the elongated handle portion 112 (and head portion 114) of surgical instrument 110 may be reusable, while the prongs 116A, 1166, 116C may be disposable and replaceable, allowing for the reuse of surgical instrument 110 in additional cataract surgeries.

It will be appreciated that the disclosed surgical instrument of the disclosed embodiments may provide for quick and efficient preliminary fragmentation of the eye lens nucleus during phacoemulsification cataract surgery, and may be safe and easy to use even by less experienced medical practitioners. Moreover, utilization of the disclosed surgical instrument may alleviate the risk of various complications associated with nucleus fragmentation, such as by protecting the posterior capsule from rupturing and minimizing stress on the zonules. The resultant fragmented nucleus is broken up into sufficiently small pieces, which simplifies and shortens the subsequent suctioning (extraction) stage. Finally, the need for expensive and bulky dedicated fragmentation equipment, such as a femtosecond laser, is averted, resulting in lowered costs and power consumption and avoiding the need to contend with potential faults and malfunctioning issues.

In accordance with embodiments, there is provided a method for fragmenting the lens nucleus of an eye. The method includes the procedure of providing an opththalmic surgical instrument that includes: an elongated handle portion, a tubular head portion, at least three prongs, an internal holding ring, and, optionally, a vibration mechanism. The head portion is disposed at a distal end of the elongated handle portion. Each of the prongs includes a cutting tip. The prongs are selectively retractable into and deployable from the head portion. The holding ring is configured to selectively contract and expand to adjust the deployment width of the prongs. The vibration mechanism is configured to selectively vibrate the prongs. The method further includes the procedure of inserting the surgical instrument toward the eye lens through a corneal incision, while opening the head portion to deploy the prongs to slide over and grasp onto the lens nucleus at a posterior position thereof. The method further includes the procedure of withdrawing the surgical instrument toward the anterior of the eye lens, while closing the head portion to retract the prongs, such that the cutting tips of the prongs cut along the lens nucleus, so as to fragment the lens nucleus into multiple segments. The vibration mechanism may be activated when the instrument is inserted toward the eye lens, to facilitate the initial penetration. The vibration mechanism may be activated during the retraction of the prongs when withdrawing the instrument away from the lens, to facilitate the cutting of the lens nucleus.

While certain embodiments of the disclosed subject matter have been described, so as to enable one of skill in the art to practice the present invention, the preceding description is intended to be exemplary only. It should not be used to limit the scope of the disclosed subject matter, which should be determined by reference to the following claims.

The invention claimed is:

1. An ophthalmic surgical instrument for fragmenting the lens nucleus of an eye, the instrument comprising:
   an elongated handle portion;
   a tubular head portion, disposed at a distal end of the elongated handle portion;
   at least three prongs, each of the prongs comprising a cutting tip, the prongs selectively retractable into and deployable from the head portion; and a holding ring, configured to selectively contract and expand to adjust a deployment width of the prongs,
   wherein the head portion and/or prongs are configured to be opened and deployed to slide over and grasp onto the lens nucleus at a posterior position thereof, and
   wherein the head portion is configured to close to retract the prongs such that the cutting tips of the prongs cut along the lens nucleus, so as to fragment the lens nucleus into multiple segments.

2. The surgical instrument of claim 1, further comprising an electromechanical units, configured to selectively vibrate the prongs, wherein the electromechanical unit is activated during at least one of:
   the insertion of the instrument toward the eye lens; and
   the withdrawal of the instrument toward the anterior of the eye lens.

3. The surgical instrument of claim 2, wherein the prongs are arc-shaped.

4. The surgical instrument of claim 2, wherein the prongs comprise a shape-memory material.

5. The surgical instrument of claim 1, wherein the prongs are arc-shaped.

6. The surgical instrument of claim 1, wherein the prongs comprise a shape-memory material.

7. A method for fragmenting the lens nucleus of an eye, the method comprising the procedures of:
   providing an ophthalmic surgical instrument comprising:
   an elongated handle portion;
   a tubular head portion, disposed at a distal end of the elongated handle portion;
   at least three prongs, each of the prongs comprising a cutting tip, the prongs selectively retractable into and deployable from the head portion; and
   a holding ring, configured to selectively contract and expand to adjust a deployment width of the prongs,
   inserting the instrument toward the eye lens through a corneal incision, while opening the head portion to deploy the prongs to slide over and grasp onto the lens nucleus at a posterior position thereof; and
   withdrawing the instrument toward the anterior of the eye lens, while closing the head portion to retract the prongs, such that the cutting tips of the prongs cut along the lens nucleus, so as to fragment the lens nucleus into multiple segments.

8. The method of claim 7, further comprising the procedure of activating an electromechanical unit of the instrument, the electromechanical unit configured to selectively vibrate the prongs, during at least one of:
   the insertion of the instrument toward the eye lens; and
   the withdrawal of the instrument toward the anterior of the eye lens.

* * * * *